(12) United States Patent
Prini

(10) Patent No.: US 6,612,185 B2
(45) Date of Patent: Sep. 2, 2003

(54) METHOD AND ASSOCIATED APPARATUS FOR MEASURING THE ADHESIVENESS OF SLOW-RELEASE TABLETS OR THE LIKE

(75) Inventor: Massimo Prini, Milan (IT)

(73) Assignee: Mipharm S.p.A., Milan (IT)

( * ) Notice: Subject to any disclaimer, the term of this patent is extended or adjusted under 35 U.S.C. 154(b) by 0 days.

(21) Appl. No.: 09/920,204

(22) Filed: Aug. 2, 2001

(65) Prior Publication Data
US 2002/0017147 A1 Feb. 14, 2002

(30) Foreign Application Priority Data
Aug. 4, 2000 (IT) ..................... MI2000A1828

(51) Int. Cl.[7] ................................. G01N 3/08
(52) U.S. Cl. ......................................... 73/827
(58) Field of Search .................. 73/835, 7, 78, 73/821, 818, 819, 824, 825, 81, 827, 830, 831, 834, 837, 842; 209/599

(56) References Cited

U.S. PATENT DOCUMENTS

| | | | | |
|---|---|---|---|---|
| 4,236,413 A | * | 12/1980 | Schmid et al. ............... | 73/821 |
| 4,346,602 A | * | 8/1982 | Gould et al. .................. | 73/842 |
| 4,393,717 A | * | 7/1983 | Mason et al. ................. | 73/821 |
| 4,472,960 A | * | 9/1984 | Motoyama et al. ............. | 73/7 |
| 4,542,646 A | * | 9/1985 | Smith et al. .................. | 73/78 |
| 6,260,419 B1 | * | 7/2001 | Kramer ....................... | 73/821 |
| 6,282,950 B1 | * | 9/2001 | Taylor et al. ............. | 73/150 A |
| 6,349,587 B1 | * | 2/2002 | Mani et al. ..................... | 73/9 |

FOREIGN PATENT DOCUMENTS

| | | |
|---|---|---|
| DE | 19603559 C | 5/1997 |
| GB | 1 351 362 | 4/1974 |
| GB | 1 394 782 | 5/1975 |
| GB | 2 151 798 A | 7/1985 |
| GB | 2 329 968 A | 4/1999 |

* cited by examiner

Primary Examiner—Max Noori
(74) Attorney, Agent, or Firm—Young & Thompson

(57) ABSTRACT

A method and related apparatus for measuring the adhesiveness of a slow-release tablet in which the tablet is adhered to a surface and a force necessary to initiate movement of the tablet parallel to the surface is measured. The measured force is used to determine the tablet's adhesiveness.

9 Claims, 2 Drawing Sheets

METHOD AND ASSOCIATED APPARATUS FOR MEASURING THE ADHESIVENESS OF SLOW-RELEASE TABLETS OR THE LIKE

BACKGROUND OF THE INVENTION

The present invention relates to a method and related apparatus for measuring the adhesiveness of slow-release tablets or the like.

In particular the method of the invention relates the use of an instrument such as a dynamometer, which is known per se, but used for different types of measurements and which allows accurate and repeatable measurements to be obtained, suitable for determining the coefficient of adhesiveness of the tablets.

In the pharmaceutical sector, there are active substances that must be assimilated very slowly over time by patients, with the result that a constant, controlled release of those substances must be provided in order to guarantee full efficacy of the substances.

For this purpose, slow-release tablets have been developed to release the active substances very slowly, for example during the course of a whole night.

These tablets, in addition to containing active substances intended for "slow release", may contain also adhesive material which allows the tablets to adhere to the mucous layer of the gums.

The properties of the adhesive material are activated when hydration occurs, namely, in the case hereunder, when the tablet comes into contact with the salival liquid present in the mouth, which enables the tablet to adhere perfectly to the mucous layer of the gums.

Since these tablets should remain attached to the gums for a very long period of time, for example overnight, without the risk of becoming detached and being swallowed while a person is sleeping, the pharmaceutical technologist must solve the problem of measuring the adhesive capacity of said tablets.

To that effect, it is necessary to resort to instruments that can measure the coefficient of adhesion, i.e. the force required to raise and separate a tablet from a surface to which it has been made to adhere, in the most precise possible manner.

The use of instruments which grip the tablet and detach it from the surface, displacing it in a direction perpendicular to the surface itself, has been proposed. However, such a proposal creates various problems, for example, how to grip the tablet firmly or to repeat the measurements with constant parameters, in most cases because the tablet cannot be detached from the surface while keeping perfectly parallel to the latter, thereby giving rise to errors in the measurement recorded.

SUMMARY OF THE INVENTION

The invention aims at overcoming the abovementioned drawbacks arising during measurement of the force needed to detach the tablet from the surface to which it adheres, by acting on the tablet in a direction tangential, rather than perpendicular, to the support surface to which the tablet adheres, namely by applying to the tablet a force which is parallel to the support surface.

For this purpose a controlled force is applied to the tablet which has been made to adhere to the surface, until the tablet starts to slip, and the force required for the tablet to start to move is measured.

For this purpose, as mentioned above, the invention envisages using a dynamometer, which is currently being used to measure the hardness of tablets, but has never been used for a purpose similar to that of the invention.

Since the force needed to cause the separation and displacement of the tablet may be related to the adhesive capacity thereof, such a force may be adopted as a parameter for precise calculation of the adhesiveness.

The objects and advantages of the invention are achieved by a method for measuring the adhesiveness of slow-release tablets. According to the proposed method, the tablet is placed on the support surface, wetted with a predetermined quantity of water, and subjected to a controlled pressure for a predetermined period of time to promote adhesion. Thereafter, a plunger is allowed to act on the tablet until the latter separates from the surface to which it had been made to adhere.

The measurement of the force required to displace the tablet can therefore be related to the adhesiveness of the tablet, which can thus be precisely measured.

BRIEF DESCRIPTION OF THE DRAWINGS

Further functions and particular features of the method and the related apparatus for measuring the adhesiveness of slow-release tablets may be better understood from the description which follows, provided herein as a non-limiting example, and reference to the accompanying drawings in which.

DESCRIPTION OF THE PREFERRED EMBODIMENT

Figure 1:
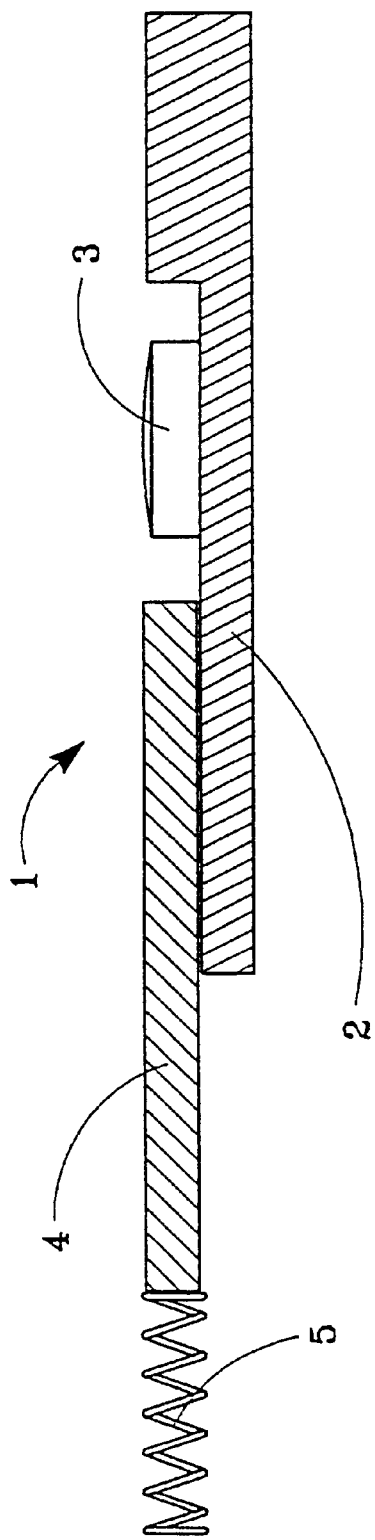
FIG. 1 shows a schematic cross-sectional view, in a vertical plane, of the measuring instrument according to the invention in its entirety.
Figure 2:
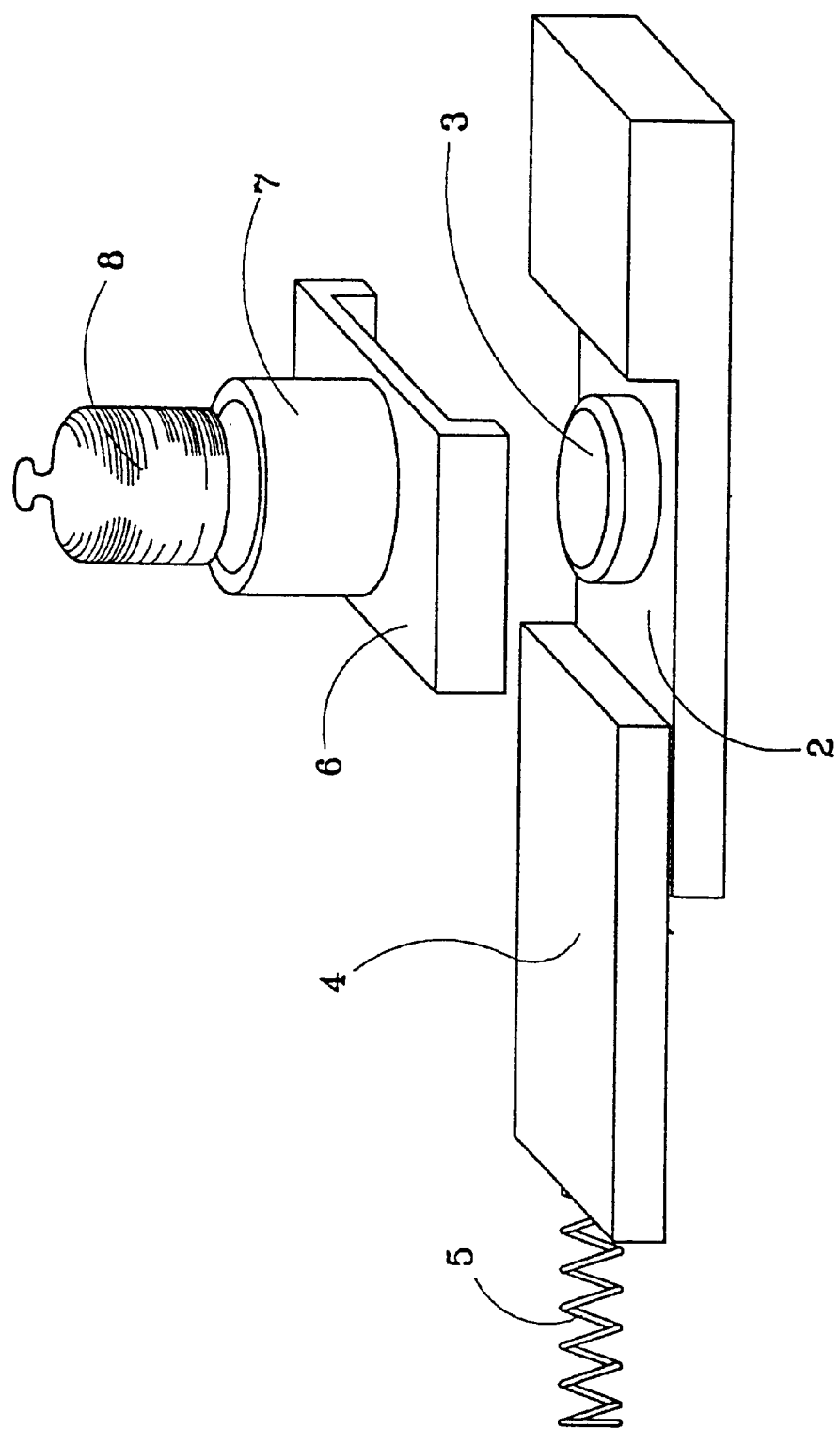
FIG. 2 shows a schematic perspective view of the instrument according to the previous figure, with the addition of the compression element.

With reference to the accompanying figures, FIG. 1 denotes in its entirety an apparatus for measuring the adhesiveness of a tablet, which comprises a support surface 2 on which the tablet 3, whose coefficient of adhesion is to be measured, is placed.

The support surface 2, which may be displaced horizontally by motor-driven systems (not shown in the figure), is moved in relation to a measuring instrument—denoted by 4—which consists of a plunger opposed to resilient means 5.

In accordance with the invention, in order to perform measurements under constant conditions, means are envisaged for pressing with a constant force the tablet against the support surface 2, after wetting it with a predetermined quantity of water.

These means comprise a support element 6 which is positioned astride the tablet support surface 2 and which in turn comprises a guide 7 inside which a calibrated weight 8 slides.

The support element 6 is positioned with the tubular guide opposite the tablet so that the weight sliding inside the guide rests against the upper side of the tablet 3.

It should be noted that the tablet 3 surface that rests on the surface 2 is flat, while its opposite side, on which the calibrated weight 8 rests, is convex.

The method according to the invention comprises the following operating steps:

the tablet 3 is placed on the support surface 2 of the measuring instrument;

the tablet 3 is wetted with a predetermined quantity of water supplied in standardised quantity;

the support element 6 is arranged astride the surface 2 supporting the tablet 3 so that the guide 7 is arranged exactly over the tablet, surrounding it;

the calibrated weight 8 is introduced into the guide 7 so that it rests on the upper surface of the tablet, and allowed to press the tablet for a predetermined period of time;

when the adhesive action promoted by the weight 8 has been fully developed, the weight and the associated support element are removed and the surface 2 is pushed against the plunger 4 of the dynamometer, which acts in opposition to resilient means such as a pre-calibrated spring 5.

The plunger pushes the tablet laterally, causing it advance together with the surface 2 against the force exerted by the spring 5 until the tablet separates from the surface 2 to which it was attached.

The measurement of the force necessary for causing displacement of the tablet, which depends on the adhesiveness of the tablet itself, may therefore be calculated exactly using parameters and under test conditions which are constant and reproducible, using the known techniques for operation of the instrument.

As may be noted, the adhesive capacity of the tablet is measured along a tangential plane, namely by applying to the tablet a force which is parallel to the plane to which it adheres, avoiding the difficulties associated with firm gripping of the tablet, separation from the surface and consequent errors in the measurement recorded.

A person skilled in the art may envisage modifications and variations, thus obtaining solutions which are also to be regarded as included within the scope of protection of the invention hereunder as defined by the following claims.

What is claimed is:

1. A method of measuring adhesiveness of a slow-release tablet to an external surface, the method comprising the steps of:

adhering a tablet to a support surface by placing the tablet on the support surface, wetting the tablet with a liquid to promote adhesion of the tablet to the support surface, and exerting a first force on the tablet perpendicular to the support surface;

applying to the tablet a second force parallel to the support surface;

measuring the applied force necessary to initiate movement of the tablet parallel to the support surface; and determining the adhesiveness of the tablet from the measured force, wherein the step of exerting the first force comprises the steps of placing a guide over the tablet, introducing a weight into the guide, and resting the weight on the tablet for a first time period.

2. The method of claim 1, wherein the liquid is water.

3. The method of claim 1, wherein the weight is removed from the tablet at the end of the first time period and before the applying step.

4. The method of claim 1, wherein the adhering step comprises the step of placing a flat surface of the tablet on the support surface.

5. The method of claim 1, wherein the measuring step is carried out with a dynamometer.

6. The method of claim 1, wherein the tablet is intact throughout the method.

7. A device for measuring adhesiveness of a slow-release tablet to an external surface, comprising:

a support surface adapted to have a tablet adhered thereto;

means for applying to the tablet a force parallel to said support surface;

means for measuring the applied force necessary to initiate movement of the tablet parallel to said support surface, where the adhesiveness of the tablet is determined from the measured force; and a guide removably positioned over said support surface and having a longitudinal axis perpendicular to said support surface, and a weight received by said guide, said weight being arranged and adapted to rest on a tablet on said support surface to adhere the tablet to said support surface.

8. The device of claim 7, wherein said means for measuring comprises a dynamometer.

9. The device of claim 7, wherein said means for applying to the tablet a force parallel to said support surface comprises a plunger that is urged in a direction parallel to said support surface by a spring.

* * * * *